United States Patent [19]

Hunziker

[11] 4,078,880

[45] Mar. 14, 1978

[54] APPARATUS FOR DETECTING NON-COMBUSTED FUEL COMPONENTS IN EXHAUST GASES OF A HEATING INSTALLATION AND METHOD FOR OPERATING THE AFORESAID APPARATUS

[76] Inventor: Richard Hunziker, Im Baumgartli 1, 4460 Gelterkinden, Switzerland

[21] Appl. No.: 702,960

[22] Filed: Jul. 6, 1976

[30] Foreign Application Priority Data

Jul. 10, 1975 Switzerland .................. 8998/75

[51] Int. Cl.² .......................................... F23M 5/08
[52] U.S. Cl. .................. 431/76; 324/65 R; 431/13
[58] Field of Search .................. 431/3, 13, 6, 32, 76, 431/5, 2; 324/65 R, 65 P

[56] References Cited

U.S. PATENT DOCUMENTS

| 3,369,588 | 2/1968 | Livingston | 431/3 |
| 3,973,898 | 8/1976 | Seider | 431/76 |

*Primary Examiner*—Edward G. Favors
*Attorney, Agent, or Firm*—Werner W. Kleeman

[57] ABSTRACT

A method of and apparatus for detecting non-combusted fuel components in exhaust gases of a heating installation comprising a collector for collecting the non-combusted fuel components. The collector is provided with a probe serving to generate an electrical signal dependent upon the quantity of collected fuel components and with an electricaly operating element for the removal of the collected fuel components.

17 Claims, 6 Drawing Figures

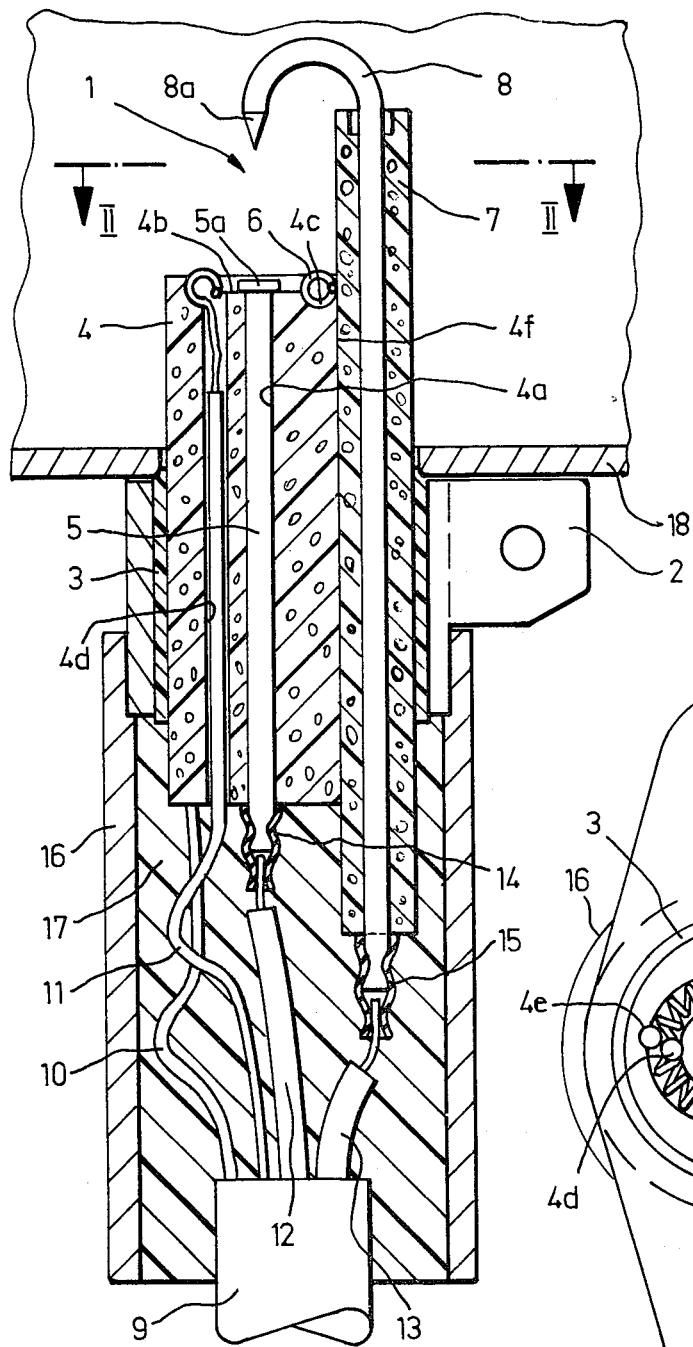
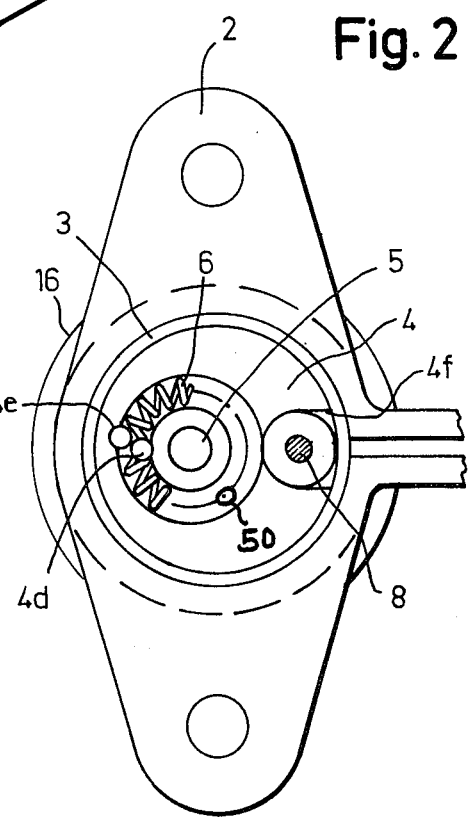
Fig. 1
Fig. 2

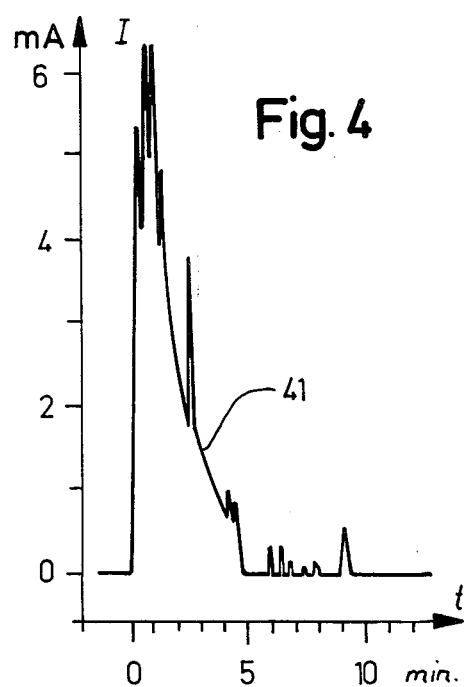
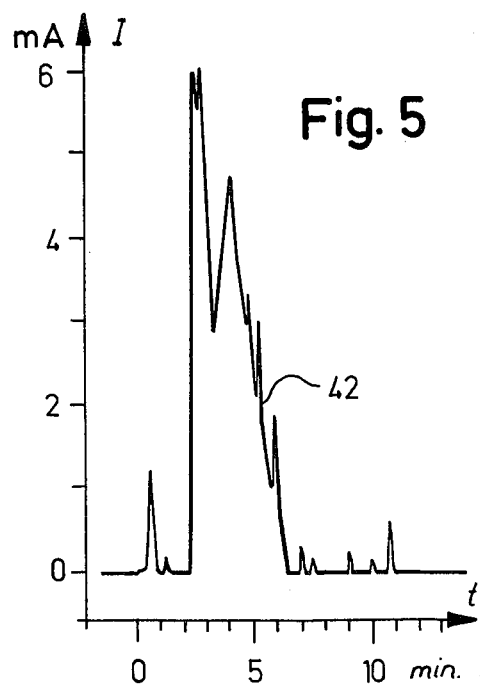
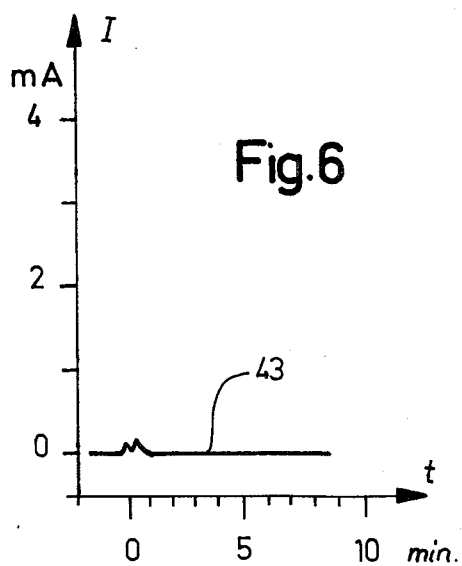

APPARATUS FOR DETECTING NON-COMBUSTED FUEL COMPONENTS IN EXHAUST GASES OF A HEATING INSTALLATION AND METHOD FOR OPERATING THE AFORESAID APPARATUS

BACKGROUND OF THE INVENTION

The present invention relates to a new and improved construction of apparatus for detecting non-combusted fuel components in exhaust gases of a heating installation and also pertains to a method for operating the aforesaid apparatus.

The efficiency of an oil heating installation is dependent to a large extent upon the adjustment of the burner and the infeed of the air. In order to realize maximum efficiency the burner should be adjusted such that there is produced an air-fuel mixture possessing an approximately stochiometric oxygen-fuel ratio or a small excess of oxygen.

If the air infeed is too small then the exhaust gases contain non-combusted carbon. On the other hand, if the air infeed is too large then the flame possesses a relatively small temperature and from the fuel there are formed from so-called crack reactions unsaturated hydrocarbons which then likewise partially escape without being burned along with the exhaust gases. In both instances the exhaust gases contain unburned or non-combusted fuel components, so that the efficiency decreases. If combustion proceeds with an excess of air then additionally the thermal yield is reduced owing to the smaller flame temperature.

Usually the burner is optimumly adjusted at the time that the heating installation is installed. However, during operation changes can occur, resulting in a deviation from the optimum conditions. For instance, it is possible that the filter in the oil infeed line, the burner head or the air suction line become clogged. Further, the draft conditions in the flue can alter due to contamination and for other reasons. These changes generally result in a decrease in the efficiency of the system. On the other hand, this leads to an increased fuel consumption and, on the other hand, to a considerable pollution of the environment. The latter is especially of significance since if there is an incomplete combustion there are also formed noxious substances, for example carbon monoxide.

Heretofore the checking of heating installation was carried out by skilled persons associated with the heating industry, for instance, chimney sweeps or other skilled mechanics who visually checked, after a longer period of operation, the deposition of carbon black and tar. Due to this visual checking it was possible to draw certain conclusions regarding the operation of the burner. Yet, such visual control is rather subjective and only possible if following each such control there are removed the deposits which have been found. Furthermore, such checking operations can only be carried out at relatively large time intervals.

Additionally, apparatuses are known to the art which consist of a suction pump and a filter head using a paper filter. In order to check the operation of the heating installation the person checking the installation during operation of the burner, sucks exhaust gases produced by the heating installation through the paper filter by means of the pump for a certain period of time. In the event that the exhaust gas contains carbon black due to an insufficient quantity of air being present during combustion then there will be produced a blackening of the filter. This can then be compared with a comparison scale and in turn there can be ascertained the content of carbon black in the exhaust gases. However, if the heating installation is operated with an excess of air then the exhaust gases do not contain carbon black, rather unsaturated hydrocarbons. Such do not blacken the paper filter rather produce a yellow coloration thereon. It is, however, hardly possible from this yellow coloration of the paper filter to somewhat exactly determine the hydrocarbon content of the exhaust gases. To arrive at a reliable quantitative determination of the quantity of hydrocarbons present in the exhaust gases there must be carried out a quantitative chemical analysis or a chromatographic test. A reliable determination of the unburned fuel components which are present in the exhaust gases by means of this state-of-the-art apparatus is therefore extremely complicated. Since to carry out a quantitative-determination there is required in any event a person making such control this type of checking of the heating installation can only be accomplished at relatively large time intervals.

SUMMARY OF THE INVENTION

It is therefore a primary object of the present invention to provide an apparatus for detecting unburned or non-combusted fuel components in the exhaust gases of a heating installation and a method for operating such apparatus, which considerably improves upon the prior art techniques and is not associated with the aforementioned drawbacks and limitations.

Another and more specific object of the invention aims at the provision of an apparatus which automates the monitoring of a heating installation and checks the quantity of non-combusted fuel components present in the exhaust gases in brief time intervals without the need for the assistance of an individual to carry out such checking operation.

Now in order to implement these and still further objects of the invention which will become more readily apparent as the description proceeds, the apparatus of this development for the detection of non-combusted fuel components in the exhaust gases of the heating installation comprises a collector for collecting the non-combusted or non-burned fuel components, the collector is provided with a probe serving to generate an electrical signal dependent upon the quantity of collected fuel components and with an electrically operating element in order to remove the collected fuel components.

As mentioned above the invention is also concerned with a method of operating the apparatus, and which method is manifested by the features that, periodically during a predetermined combustion duration of the heating installation fuel components are collected by means of the collector and by means of the probe there is produced a signal dependent upon the quantity of fuel components, and the collected fuel components are removed.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a longitudinal sectional view through an electro-filter having a probe for measuring the collected fuel components;

FIG. 2 is a cross-sectional view taken substantially along the line II—II of FIG. 1;

FIG. 4 is a graph showing the time course of the probe-current when the filter has deposited thereon pure carbon;

FIG. 5 is a graph illustrating the time course of the probe-current when the filter has deposited thereon hydrocarbon compounds; and FIG. 6 is a graph illustrating the time course of the probe-current after filtering the exhaust gases produced by an optimumly adjusted burner.

DETAILED DESCRIPTION OF THE INVENTION

Figure 3:
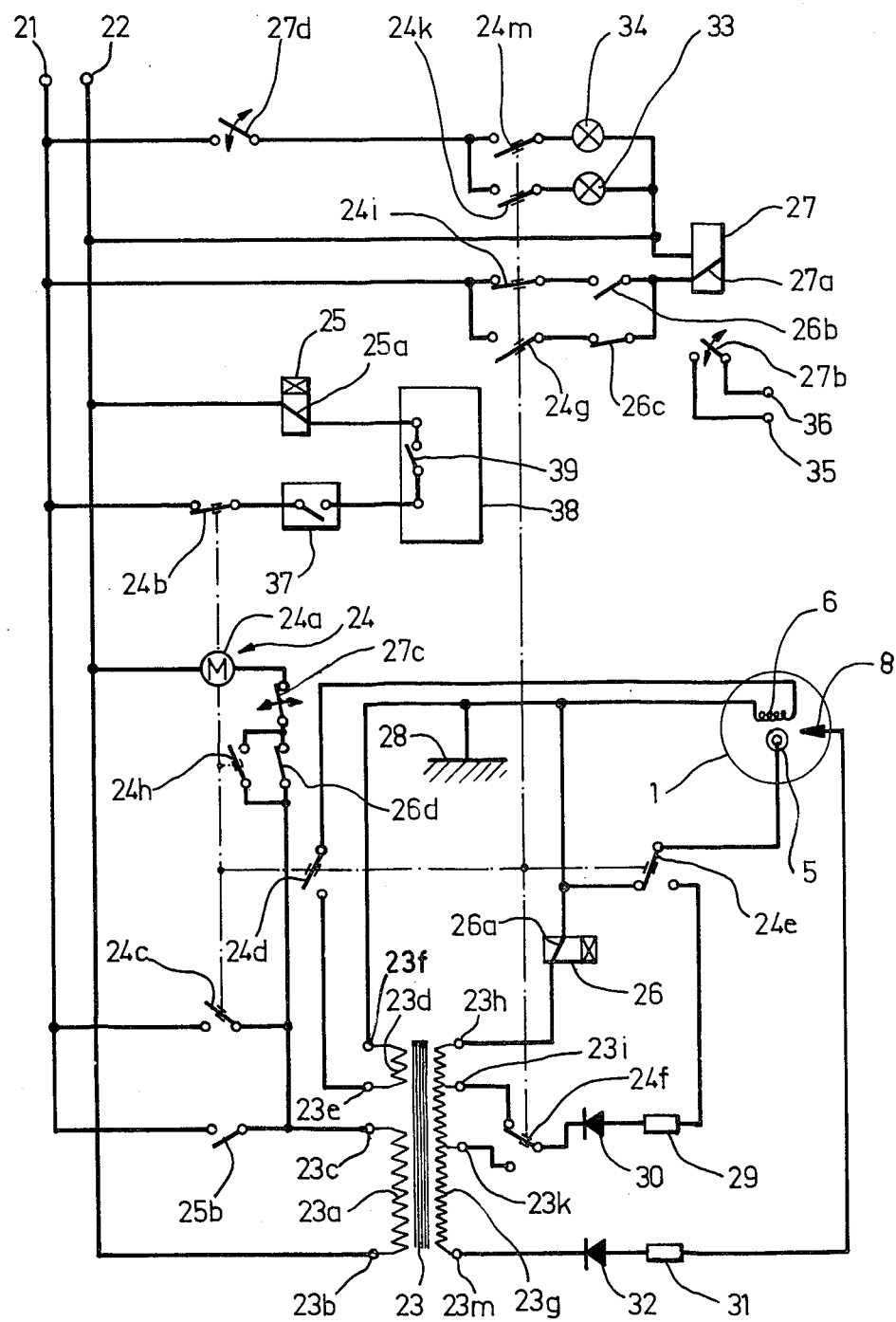
FIG. 3 is an electrical circuit diagram of the apparatus.

Describing now the drawings the exemplary embodiment of apparatus for detecting non-combusted fuel components as shown in FIGS. 1 and 2 will be seen to comprise an electro-filter 1. This electro-filter 1 possesses a clampable flange 2 which can be secured by means of screws or other suitable fastening expedients at the wall 18 of an exhaust gas channel or a combustion chamber of an oil heating installation. At the flange 2 there is secured a ceramic insulating body 4 encapsulated by an asbestos collar 3. The insulating body 4 is provided with a continuous, eccentric longitudinal bore 4a and at one end face with a countersunk bore coaxial to the longitudinal bore 4a, and wherein the floor surface or bottom of such countersunk bore has been designated by 4b. The outer edge of the bottom surface 4b is formed by a somewhat deeper groove 4c having an arcuate-shaped cross-sectional configuration, as best seen by referring to FIG. 1. The insulating body 4 is furthermore equipped with two open-ended or continuous longitudinal bores 4d and 4e which open into the groove 4c. This insulating body 4 will be seen to possess at the side of the outer surface which faces away from the longitudinal bore 4a a longitudinal groove 4f which in cross-section possess a substantially U-shaped configuration.

Inserted into the longitudinal bore 4a is an electrode 5 having a head 5a which bears upon the bottom or floor surface 4b. In the groove 4c there is arranged a heating resistor 6 formed by a helical-shaped wire and likewise bearing at the insulating body 4. A cylindrical ceramic tube 7 having an electrode 8 is secured in the longitudinal groove 4f. The free end of the electrode 8 has a semi-circular shaped curvature and is equipped with a tip 8a confronting the head 5a of the electrode 5.

The end of the insulating body 4 which is located at the top of FIG. 1, the head 5a of the electrode 5, the heating resistor or resistance 6 as well as the tip 8a of the electrode 8 extend into the exhaust gas channel bounded by the wall 18 so that exhaust gases flow around such components during operation of the heating installation.

Both ends of the heating resistor-wire 6 are connected through the agency of the bores 4d, 4e with the strands or wires 10 and 11 of a cable 9. The electrode 5 is connected by means of a coupling or clamp 14 with the strand 12 and the electrode 8 by means of a coupling or clamp 15 with the strand 13 of the cable 9. Attached to the flange 2 is a sleeve or collar 16 into which piercingly extends the cable 9 and into which there is molded a suitable insulating molding or casting mass 17.

FIG. 3 illustrates the electrical circuit diagram of the apparatus in which reference character 1 again designates the already described electro-filter. As to such filter there have been shown in the electrical circuit diagram the electrodes 5 and 8 as well as the heating resistor 6.

Reference characters 21 and 22 designate the two terminals of a power supply and reference character 23 a transformer having a primary winding 23a. The terminals of the primary winding have been designated by reference characters 23b and 23c. The transformer further includes a low-voltage secondary winding 23d having two terminals 23e, 23f and a high-voltage secondary winding 23g. Such incorporates two end terminals 23h, 23m and intermediate thereof two taps 23i, 23k.

Continuing, the apparatus further comprises a program-switching drum 24 provided with a drive motor 24a and 10 switching contacts 24b, 24c, 24d, 24e, 24f, 24g, 24h, 24i, 24k, and 24m. Additionally, there is provided a relay 25 which responds with a time-delay and having a coil 25a and a closing contact 25b. A further likewise time-delay responsive relay 26 possesses a coil 26a, a closing contact 26b and two opening contacts 26c, 26d. A relay 27 possesses a coil 27a and three contacts 27b, 27c, 27d equipped with a conventional mechanical locking device.

The heating resistor 6 is connected with both of the terminals 23e, 23f of the transformer-secondary winding 23d and additionally with the housing-ground 28. The electrode 5 is connected by means of the reversing or switching contact 24e either with the housing-ground 28 or via a resistor 29 and a rectifier 30 with a terminal of the switching contact 24f. Both of the other terminals of this switching contact are connected with the terminals 23i and 23k of the secondary winding 23g. The electrode 8 is connected by means of a resistor 31 and a rectifier 32 with the terminal 23m of the secondary winding 23g. The terminal 23b of the transformer-primary winding 23a is connected with the terminal 22 of the network connection or power supply. The other primary winding-terminal 23c is connected by means of two parallel connected switching contacts 24c, 25b with the network terminal 21 and by means of both likewise parallelly connected switching contacts 24h, 26d and the switching contact 27c with one of the terminals of the motor 24a of the program-switching drum 24. The other terminal of the motor 24a is connected with the network or main terminal 22.

Further the apparatus possesses an indicator or alarm lamp 33 or equivalent structure of which the one terminal is connected with the network terminal 22 and the other terminal is connected via the switching contacts 24k and 27d with the network terminal 21. The interconnected terminals of the switching contacts 24k and 27d are furthermore connected via the switching contact 24m with the one terminal of a disturbance indicating lamp 34, the other terminal of which is coupled to the terminal 22 of the power supply network. The closing contact 27b is connected with two conductor terminals 35, 36.

In the electrical circuit diagram of FIG. 3 there will be further recognized a thermo-switch 37 and a control unit or device 38 having a switch 39 and serving to control the oil burner. The coil 25a of the relay 25 is connected at one end with the network terminal 22 and at the other end via the switch 39, the thermo-switch 37 and the switch 24b with the network terminal 21.

Having now had the benefit of the foregoing description of the exemplary embodiment of the apparatus of this invention its operation will be considered and is as follows:

The burner of the heating installation initially is not in operation, the program-switching drum 24 is located in its starting position and the three relay coils 25a, 26a and 27a all do not carry any current. The switching contacts of the program-switching drum 24 and the relays 25, 26 and 27 are then located in the position shown in FIG. 3.

Now when the temperature drops below the adjusted value then the thermo-switch 37 is closed. By means of not particularly illustrated but conventional elements of the control device 38 there is initially turned-on the air infeed device and during a predetermined time interval there is carried out an air pre-flushing operation. Then the infeed of oil is initiated, the burner fired and the switch 39 closed. The relay 25, following a response delay of for instance two seconds, is energized and hence the closing contact 25b is closed. Consequently, the motor 24a of the switching drum is placed into operation and current is supplied to the primary winding 23a of the transformer 23. Between the winding terminals 23h and 23m there then appears a voltage of about 5000 volts. As a result the electro-filter is now placed into operation. Since the terminal 23h of the transformer winding 23g is connected via the relay coil 26a with the heating resistor 6 and via the switching or reversing contact 24e additionally with the electrode 5, there are present between the electrode 8 and the electrode 5 as well as the heating resistor 6 corona discharges. In the event that the exhaust gases produced by the burner contain non-combusted fuel components then due to the corona discharges such will be deposited and collected at the electrode 5 at the heating resistor 6 and at surface 4b of the insulating body 4. This working phase therefore will be referred to hereinafter as the collecting phase.

The program-switching drum is constructed in such a manner that all switching contacts 24b, 24c, 24d, 24e, 24f, 24g, 24h, 24i, 24k, 24m remain in the illustrated position during, for instance, 100 hours of operation of the motor 24a. During this time duration there thus is collected the unburned or non-combusted fuel components. Upon switching-off the burner the motor 24a also is at standstill. Therefore, independent of the length of the individual time intervals during which the burner is operational there will be always collected fuel components throughout a total burner-operation duration of 100 hours.

After the expiration of the 100 hours of operation of the burner the contact 24b is opened and the burner placed out of operation. Further, the contacts 24c, 24d, 24k are closed and the contact 24e switched. Hence there now begins the phase of operation hereinafter termed the measurement phase. During such the heating resistor 6 is heated and between the electrode 5 and the heating resistor 6 there appears a pulsating direct-current voltage. The transformer 23 thus forms a supply device which serves the purpose of delivering current to the heating resistor 6 and producing a voltage between the electrode 5 and the heating resistor 6. If there have been deposited non-combusted fuel components upon the surface 4b of the electro-filter 1, then a leakage current flows between the electrode 5 and the heating resistor 6.

In the exemplary embodiment under discussion the alternating-current voltage between the transformer terminals 23h and 23i amounts to about 1000 volts. The size of the resistor 29 is chosen such that the current is limited to about 6.5 mA for a direct conductive connection between the electrode 5 and the heating resistor 6.

FIGS. 4 to 6 illustrate typical examples for the time progression of the leakage current for different types of filter depositions. In the three figures just mentioned reference character I designates the leakage current and reference character t the time after applying the voltage between the electrode 5 and the heating resistor 6 with simultaneous switching on of the heating.

The curve 41 of FIG. 4 illustrates a typical example for the time progression of the leakage current I when the collecting surface 4b of the electro-filter I has deposited thereon flaky carbon black, i.e. pure carbon. Upon switching-in the heating resistor 6 there occurs heating of the collected carbon. This is further intensified by the leakage current flowing through the carbon. Due to such heating the conductivity of the carbon increases and therefore also the leakage current I. After about 30 seconds or a whole minute the leakage current approximately reaches the maximum possible value of about 6.5 mA. The carbon now is still further heated by the heating resistor and the leakage current, so that it begins to burn. This combustion results in the leakage current again decreasing and after about 5 minutes reaching the value null.

In the time interval extending from $t=5$ minutes to $t=10$ minutes there still occur individual brief current surges. If the value of $t$ is greater than about 10 to 15 minutes then these also disappear. This means that the collected carbon has completely burned and thus has again been removed from the filter.

Curve 42 of FIG. 5 shows the time progression or time course of the leakage current in the case where the filter surface 4b has been predominantly contaminated with hydrocarbons, for instance with shining soot or lampblack. Hydrocarbons are essentially electrically non-conductive materials. In the first 2 minutes after applying the voltage there thus only occur individual small voltage spikes which apparently are attributable to the presence of carbon. Due to the heating by the heating resistor the hydrogen is however successively split-off from the hydrocarbons. This results in the formation of a conductive carbon layer, so that the leakage current after about 2 to 3 minutes likewise can approximately reach the maximum possible value. The further course of the curve is then similar to that discussed above with respect to FIG. 4.

After approximately 50 hours of operation of an optimumly adjusted burner there was measured a leakage current having the time course shown by curve 43 of FIG. 6. The leakage current in this case is smaller than about 0.2 mA throughout the entire time that the voltage was switched-on.

The electrode 5 and the heating resistor 6 thus collectively form a probe 5,6 which renders possible producing a signal, namely the leakage current I which changes as a function of time, and which signal is dependent upon the quantity of non-combusted, collected fuel components. The magnitude of the leakage current I is thus determined by the specific conductivity of the fuel components collected by the electro-filter 1. The heating resistor 6 not only serves however for producing the leakage current, rather, as described, also has an electrically operating element for the combustion and removal of the collected fuel components. For this purpose the heating resistor is advantageously heated to such an intensity that it begins to glow.

The leakage current I flows through the coil 26a of the relay 26. If the current as shown in FIGS. 4 and 5 exceeds a value of about 2 mA then such relay, following a time-delay of for instance 2 seconds is energized. Due to the response delay of the relay there is avoided that the relay already will respond during short-time current surges, as such for instance could arise during spark discharges. If the relay 26 responds, then the contact 26b is closed and the contacts 26c, 26d are opened. Closing of the contact 26b results in energization of the relay 27 and the contacts 27b and 27d are closed, so that the lamp 33 illuminates and thus produces an alarm signal. The conductor terminals 35, 36 can be for instance connected via a conductor with an alarm transmitter located in another room.

Since during response or energization of the relays 26 and 27 the contacts 26d and 26c are opened, the current supply to the motor 24a is interrupted and the program-switching drum remains stationary until the relay 27 is manually released. Since the contact 24b is open during the measurement phase, there is prevented in the presence of an alarm also the further operation of the burner. The heating resistor 6 in the meantime is continuously heated, so that the collected fuel components burn and the relay 26 again is de-energized. If the relay 27 is released, then the program-switching drum again is placed into operation and the program proceeds in a normal manner. The relays 26 and 27 thus form a monitoring device which monitors the leakage current and, if such exceeds a predetermined value, triggers an alarm signal and blocks further operation of the burner.

If the leakage current arising during the measurement phase is not sufficient to actuate the relay 26, then of course, no alarm signal is produced and the program-switching drum 24 runs on continuously. After a predetermined time of, for instance 10 minutes the contact 24f is switched, the contacts 24h and 24m are closed and the contacts 24i and 24k are opened. As a result there is initiated the testing phase. The electrode 5 now has delivered thereto a voltage which is considerably greater than that prevailing during the measurement phase. The magnitude of this voltage is calculated such that there occurs a gas discharge between the electrode 5 and the heating resistor 6 in the event that such is still heated. The thus flowing current causes the relay 26 to be energized. Now since the contact 24h is closed the motor 24a will continue to run notwithstanding opening of the contact 26d.

Furthermore, since the contacts 24i and 24k are now open, there is also no triggering of any alarm signal. Now with a predetermined delay there is still closed the contact 24g. If the relay 26, as previously described, has responded upon switching of the contact 24f and thus has opened the contact 24c, then the program will continue to run in its normal course. On the other hand, if the heating resistor 6 is defective or the infeed line leading thereto or to the electrode 5 is interrupted then upon switching of the contact 24f there does not occur any gas discharge and the relay 26 does not respond. Upon closing of the contact 24g the relay 27 then responds and is locked. This results in the current infeed to the motor 24a being interrupted and that the lamp 34 illuminates and thus there is produced a disturbance or fault indication.

Now in order that the program-switching drum 24 continues to run further, it is necessary that the relay 27 is manually released just as was the case during triggering of an alarm. By means of the testing phase there is completed the work cycle and the program-switching drum again reaches its starting position. Now the burner can be again placed into operation and there can be initiated a collecting phase.

The gas discharge carried out during the testing phase has still a further purpose. It is possible that the exhaust gases also contain non-combustible, inorganic solids, for instance dust emanating from the furnace lining. Since such solids will not burn upon switching-in the heating resistor 6 they could constitute a permanent contamination for the filter. Tests with asbestos dust being applied to the filter have shown that such type non-combustible solids can be removed during the gas discharge by the prevailing gas currents.

During operation of the apparatus there are alternately collected unburned or non-combusted fuel components by means of the filter serving as a collector during a predetermined combustion duration of the heating installation and there is produced a signal dependent upon the quantity of the collected fuel components. Further by combustion of the fuel components the filter is again cleaned simultaneous with the generation of the signal or subsequent thereto. By means of the apparatus it is thus possible to approximately continually monitor the content of the exhaust gases with respect to carbon and hydrocarbons. If the content has exceeded a predetermined value and triggered an alarm signal then the owner of the building where the heating installation is installed or the building engineer can have the burner readjusted. Corresponding measures of course must be taken upon the occurrence of a disturbance report in order to overcome the cause of the disturbance.

Placing of the burner out of operation which occurs following the occurrence of an alarm signal provides a certain assurance that the readjustment of the burner will not be forgotten. The apparatus furthermore can be provided with an additional blocking mechanism which, for instance, after the occurrence of three successive alarm- or disturbance reports blocks the further operation in such a manner that the heating installation can only be again placed into operation by an authorized individual, such as a skilled service man, for instance after there has been removed a security seal.

Of course the apparatus can be modified with respect to a number of different aspects. For instance, the filter can be provided with an additional electrode, such as the electrode 50 shown in FIG. 2, contacting the surface 4b serving to collect the fuel components. During the measurement phase there could be then measured or monitored the current flowing between this additional electrode 50 and the electrode 5. Moreover, it would also of course be possible to determine the resistance of the fuel components in that there is impressed a constant current and there is determined the voltage needed to produce the same. In this instance an alarm signal then would be triggered if the voltage falls below a predetermined boundary value.

Since the surface of the heating resistor 6 is conductive and accessible from the outside, and since during the collecting phase also the heating resistor is covered with non-burned fuel components, there also is altered its inherent specific conductivity as a function of the fuel components contained in the exhaust gases. Such fuel components then could be thus detected in that by means of a suitable element there is produced a signal depending upon the conductivity of the heating resistor which in this case serves as the collector. If the system is operated with a constant heating voltage then the heating current can be monitored by means of a relay.

Additionally, it would be possible to provide a temperature feeler or sensor instead of the electrode 5. During the measurement phase there could be determined the temperature increase occurring upon combustion of the collected fuel components. Hence, the electrode 5 also therefore in this case may conceptually considered as such temperature feeler.

Further, instead of an electro-filter there could be used a ceramic filter at which the exhaust gases must flow through a porous ceramic body upon which there can deposit the fuel components.

As a matter of simplicity in the disclosure and discussion reference has been made only as a matter of convenience to heating installations. Yet it is expressly to be understood that under such term there is encompassed all types of heating systems of any kind where there is employed an oil or fuel burner.

While there is shown and described present preferred embodiments of the invention, it is to be distinctly understood that the invention is not limited thereto, but may be otherwise variously embodied and practiced within the scope of the following claims.

What is claimed is:

1. An apparatus for detecting non-combusted fuel components in the exhaust gases of a heating installation, comprising a collector for collecting the non-combusted fuel components, probe means provided for the collector for periodically generating an electrical signal dependent upon an electrical characteristic of the collected fuel components, said electrical signal being representative of the quantity of collected fuel components and an electrically operating element for removing the collected fuel components.

2. The apparatus as defined in claim 1, wherein the electrically operating element constitutes part of the probe means.

3. The apparatus as defined in claim 1, further including a monitoring device in order to at least produce an alarm signal when the signal produced by said probe means deviates from a predetermined boundary value.

4. The apparatus as defined in claim 1, further including a monitoring device for initiating blocking of further operation of the burner of the heating installation when the signal produced by the probe means has deviated from a predetermined boundary value.

5. The apparatus as defined in claim 1, further including a program-control element for switching-on the probe means and the element for removing the collected non-combusted fuel components after a predetermined operating time of the heating installation.

6. A method of detecting non-combusted fuel components in the exhaust gases of a heating installation comprising the steps of:
   a. collecting by means of a collector the non-combusted fuel components present in the exhaust gases produced by a heating installation;
   b. collecting the non-combusted fuel components during a predetermined combustion duration of the heating installation by means of the collector;
   c. producing an electrical signal dependent upon an electrical characteristic of the collected fuel components, said characteristic being representative of the quantity of collected fuel components; and
   d. removing the collected fuel components.

7. A method of detecting non-combusted fuel components in the exhaust gases of a heating installation comprising the steps of:
   a. collecting by means of a collector the non-combusted fuel components present in the exhaust gases produced by a heating installation;
   b. collecting the non-combusted fuel components during a predetermined combustion duration of the heating installation by means of the collector; and
   c. producing an electrical signal dependent upon the electrical conductivity of the collected fuel components, said conductivity being representative of the quantity of collected fuel components.

8. An apparatus for detecting non-combusted fuel components in the exhaust gases of a heating installation, comprising a collector for collecting the non-combusted fuel components, said collector comprising an insulating body having a collecting surface serving for collection of the non-combusted fuel components, probe means provided for the collector for producing an electrical signal dependent on the quantity of collected fuel components, said probe means including a heating resistor having a conductive surface and an electrode, said electrode and conductive surface contacting the collecting surface of the insulating body, a supply means delivering current to the heating resistor for generating said electrical signal which is dependent upon the conductivity of the collected fuel components located between the electrode and the heating resistor, and for removing the collected fuel components.

9. An apparatus for detecting non-combusted fuel components in the exhaust gases of a heating installation, comprising a collector for collecting the non-combusted fuel components, said collector comprising an insulating body having a collecting surface for collecting the non-combusted fuel components, an electrically operating element for removing the collected fuel components, probe means provided for the collector for producing an electrical signal dependent upon the quantity of collected fuel components, said probe means comprising first and second electrodes contacting said collecting surface, said electrically operating element comprising a heating resistor, and means furnishing the heating resistor with power for generating said electrical signal which is dependent upon the conductivity of the collected fuel components located between the first and second electrodes.

10. An apparatus for detecting non-combusted fuel components in the exhaust gases of a heating installation, comprising a collector for collecting the non-combusted fuel components, said collector comprising an electro-filter, probe means provided for the collector for producing an electrical signal dependent upon the quantity of collected fuel components and an electrically operating element for removing the collected fuel components.

11. An apparatus for detecting non-combusted fuel components in the exhaust gases of a heating installation, comprising a collector for collecting the non-combusted fuel components, probe means provided for the collector for producing an electrical signal dependent upon the quantity of collected fuel components, an electrically operating element for removing the collected fuel components, said probe means comprising a heating resistor having a conductive surface accessible from the outside and arranged in such a manner that during operation of the heating installation, non-combusted fuel components collect at the conductive surface, means for delivering current to the heating resistor and at least one element for producing a signal dependent upon the resistance value of the heating resistor.

12. An apparatus for detecting non-combusted fuel components in the exhaust gases of a heating installation, comprising a collector for collecting the non-combusted fuel components, probe means provided for the collector for producing an electrical signal dependent upon the quantity of collected fuel components, said probe means including a temperature feeler and an electrically operating heating resistor for removing the collected fuel components by heating and post-combustion of the collected, non-combusted fuel components.

13. A method of detecting non-combusted fuel components in the exhaust gases of a heating installation comprising the steps of:
   collecting by means of a collector the non-combusted fuel components present in the exhaust gases produced by a heating installation;
   collecting the non-combusted fuel components during a predetermined combustion duration of the heating installation by means of the collector;
   producing a signal dependent upon the quantity of collected fuel components; and
   removing the collected fuel components by burning such components.

14. A method of detecting non-combusted fuel components in the exhaust gases of a heating installation comprising the steps of:
   collecting by means of a collector the non-combusted fuel components present in the exhaust gases produced by a heating installation;
   collecting the non-combusted fuel components during a predetermined combustion duration of the heating installation by means of the collector;
   producing a signal dependent upon the quantity of collected fuel components, said producing step including heating the fuel components to convert electrically non-conductive portions thereof into conductive fuel components and determining the electrical conductivity of the collected fuel components; and
   removing the collected fuel components.

15. A method of detecting non-combusted fuel components in the exhaust gases of a heating installation comprising the steps of:
   collecting by means of a collector the non-combusted fuel components present in the exhaust gases produced by a heating installation;
   collecting the non-combusted fuel components during a predetermined combustion duration of the heating installation by means of the collector;
   producing a signal dependent upon the quantity of collected fuel components;
   removing the collected fuel components by combustion thereof and producing a gas discharge following the combustion of the collected fuel components.

16. The apparatus as defined in claim 1, wherein said electrical characteristic is electrical conductivity.

17. The method as defined in claim 6, wherein said electrical characteristic is electrical conductivity.

* * * * *